(12) United States Patent
Hasegawa et al.

(10) Patent No.: US 6,388,116 B1
(45) Date of Patent: May 14, 2002

(54) NEAR INFRARED ABSORBING COMPOUND

(75) Inventors: Shun Hasegawa; Gen Masuda, both of Chiba (JP)

(73) Assignee: Nisshinbo Industries, Inc., Tokyo (JP)

( * ) Notice: Subject to any disclaimer, the term of this patent is extended or adjusted under 35 U.S.C. 154(b) by 0 days.

(21) Appl. No.: 09/661,861

(22) Filed: Sep. 14, 2000

(30) Foreign Application Priority Data

Sep. 28, 1999 (JP) .......................... 11-274758

(51) Int. Cl.$^7$ .......................... C07F 9/08; C07F 19/00
(52) U.S. Cl. .......................... 556/24; 562/8
(58) Field of Search .......................... 556/24; 562/8; 558/70

(56) References Cited

U.S. PATENT DOCUMENTS

| | | | |
|---|---|---|---|
| 4,824,661 A | * 4/1989 | Wagner e tal. | 424/52 |
| 5,037,634 A | * 8/1991 | Williams et al. | 424/49 |
| 5,211,940 A | * 4/1993 | Ishiguro et al. | 424/49 |
| 5,286,479 A | 2/1994 | Garlich et al. | |

FOREIGN PATENT DOCUMENTS

| | | |
|---|---|---|
| JP | 55142045 | 11/1980 |
| JP | 63-116625 | 5/1988 |
| JP | 63-116626 | 5/1988 |
| JP | 6-73197 | 3/1994 |
| JP | 06118228 | 4/1994 |
| JP | 10152598 | 6/1998 |
| JP | 10 153964 | 9/1998 |

OTHER PUBLICATIONS

CA:111:53018 abs of J Inor Biochem by Martin et al 35(4) pp 267–88 1989.*
CA:101:189850 abs of Med Nutr by Lepen 20(2) pp 1130117 1984.*
CA:109:23220 abs of J Inorg Biochem by Evans J Inorg Biochem 32(4) pp 259–68 1988.*
CA:109:23220 abs of J Inorg Biochem by Evans et al 32(4) pp 259–68 1988.*
Champange, E. T., et al., "Independent and Mutal Interactions of Copper (II) and Zinc Ions with Phytic Acid", J. of Inorganic Biochemistry, vol. 30, pp. 15–33, (1987).
Martin C. J., et al., "Phytic Acid: Divalent Cation Interactions. III. A Calorimetric and Titrimetric Study of the Dependence of Copper(II) Binding", J. of Inorganic Biochem. vol. 28, pp. 39–55, (1986).
Martin, C.J., et al., "Phytic Acid: Divalent Cation Interactions. IV. A Spectroscopic Determination of CO(II) and Cu(II) Binding", J. of Inorganic Biochem. vol. 29, pp. 241–248 (1987).

* cited by examiner

*Primary Examiner*—Jean F. Vollano
(74) *Attorney, Agent, or Firm*—Kilpatrick Stockton LLP

(57) ABSTRACT

By forming a copper salt of phytic acid at a molar ratio of copper ion ($Cu^{2+}$) to phytic acid of 2:1 or higher, there is provided a compound absorbing near infrared rays, which does not substantially absorb lights of visible light wavelength range, but strongly absorb lights of near infrared wavelength range, and shows extremely good water solubility.

3 Claims, 1 Drawing Sheet

NEAR INFRARED ABSORBING COMPOUND

BACKGROUND OF THE INVENTION

1. Field of the Invention

The present invention relates to a novel substance that efficiently absorbs lights of near infrared wavelength range.

2. Description of the Related Art

Materials that absorb lights of near infrared wavelength range are utilized as heat ray absorbers or optical filters.

Various materials including those mentioned below have been examined so far.

For example, metal iron oxides such as ferrous oxide are known to absorb heat rays. However, since their absorption coefficient is considerably low, and they suffer from a problem of poor solubility in solvents. Therefore, they are not practically useful. Further, copper carboxylates as organic copper salts such as copper benzoate, copper acetate and copper naphthenate are also known to absorb heat rays. However, they have a maximum absorption wavelength of around 600–750 nm, and they only show weak absorption in near infrared range.

It has also been reported that a water-based solution added with ferrous sulfate or ferrous ammonium sulfate absorbs lights of near infrared wavelength range (Japanese Patent Laid-open (Kokai) Nos. 63-116625/1988, Japanese Patent Laid-open (Kokai) Nos. 63-116626/1988). However, if a solution of these sulfates is left for a while, they react with water to generate deposition or precipitation. Therefore, they suffer from a problem of troublesome handling, i.e., a suitable amount of sulfuric acid must be added to the solution in order to avoid such deposition or precipitation.

It is noted that phthalocyanine and naphthalocyanine are known as copper-containing organic compounds absorbing near infrared-rays. However, both of these show absorption in visible light range. Further, they have a maximum absorption wavelength of 800 nm or shorter with a sharp peak, and hence they do not show absorption in broad wavelength range.

Furthermore, there has been proposed an optical filter absorbing lights of near infrared range, characterized in that it comprises a copolymer obtained by copolymerizing a monomer with a specific structure having a phosphoric acid group and a monomer copolymerizable with the former monomer, and a metal salt mainly consisting of a copper salt (Japanese Patent Laid-open (Kokai) No. 6-118228/1994). There have also been proposed a near infrared absorbing resin composition comprising a resin obtained by polymerizing a monomer having an unsaturated double bond, a phosphorus atom-containing compound with a specific structure and copper hydroxide, and a near infrared absorbing resin composition comprising a phosphorus atom-containing compound with a specific structure (Japanese Patent Laid-open (Kokai) Nos. 10-152598/1998 and 10-153964/1998). Although these compositions absorb lights of near infrared wavelength range, they suffer from a problem of low water solubility.

SUMMARY OF THE INVENTION

An object of the present invention is to provide a compound absorbing near infrared rays, which does not substantially absorb lights of visible light wavelength range, but strongly absorb lights of near infrared wavelength range, and shows extremely good water solubility.

The inventors of the present invention assiduously studied in order to achieve the aforementioned object. As a result, they found that a copper salt of naturally occurring phytic acid strongly absorbs lights of near infrared wavelength range, and thus accomplished the present invention.

That is, the present invention provides the followings.

(1) A copper salt of phytic acid, which is formed from copper ion ($Cu^{2+}$) and phytic acid at a molar ratio of copper ion to phytic acid of 2:1 or higher.

(2) The copper salt of phytic acid according to (1), which is obtainable by reacting an inorganic copper salt or an organic copper salt with phytic acid.

(3) The copper salt of phytic acid according to (2), wherein the organic copper salt is a copper salt of a C2–C8 carboxylic acid.

(4) A near infrared absorber comprising a copper salt of phytic acid according to any one of (1) to (3).

BRIEF EXPLANATION OF THE DRAWING

Other objects and advantages of the present invention will become apparent during the following discussion in conjunction with the accompanying drawing, in which.

DETAILED DESCRIPTION OF THE EMBODIMENTS

Figure 1:
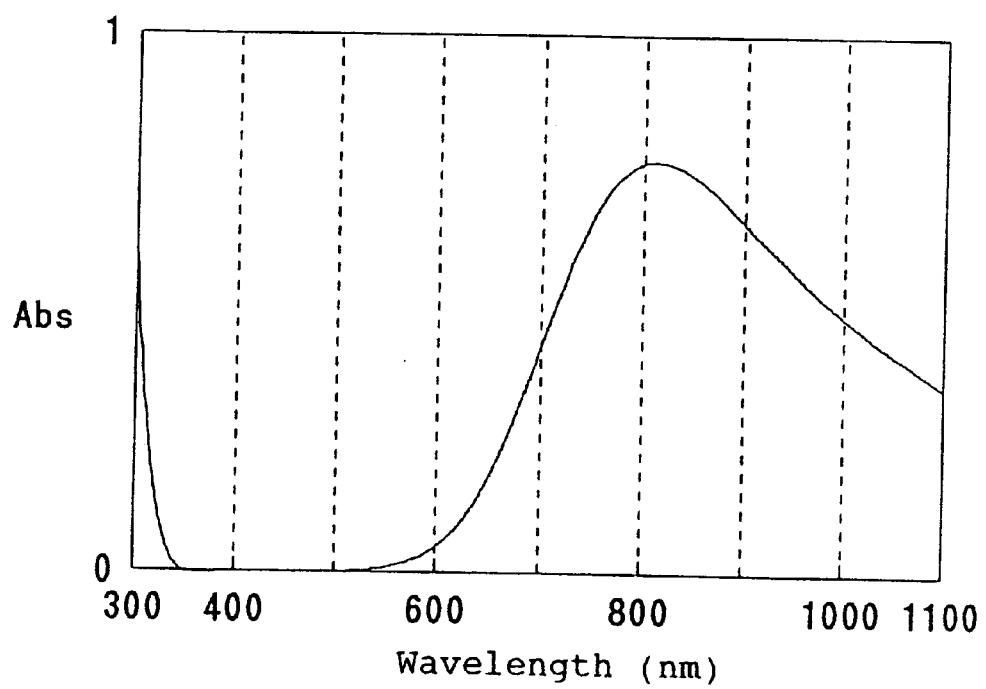
FIG. 1 represents an absorption spectrum of a compound of the present invention.

Hereafter, the present invention will be explained in more detail.

<1> Copper Salt of Phytic Acid

Phytic acid exists in nature, and it is a compound corresponding to myoinositol of which six hydroxyl groups are substituted with phosphoric acid groups ($—P(O)(OH)_2$). In the present invention, phytic acid may include those compounds partially dephosphorylated, and the term "phytic acid" is used to encompass such a substance.

As the aforementioned phytic acid, commercially available one may be used. For example, 50% phytic acid (Tokyo Kasei Co., Ltd.) can be used, which also contains phytic acid partially dephosphorylated.

The copper salt of phytic acid is formed by substitution of one mole of copper ions ($Cu^{2+}$) for the two hydrogen atoms of phosphoric acid groups in 1 mole of phytic acid. In the present invention, a copper salt of phytic acid in which copper ions ($Cu^{2+}$) and phytic acid form a salt at a molar ratio of 2:1 or higher means a salt formed with 1 mole of phytic acid and 2 moles or more of copper ions ($Cu^{2+}$). That is, when the copper salt is formed with 1 mole of phytic acid and 2 moles of copper ions ($Cu^{2+}$), four hydrogen atoms of the phosphoric acid groups in the phytic acid molecule is substituted with two copper ions ($Cu^{2+}$).

The molar ratio of phytic acid:copper ions ($Cu^{2+}$) may be 1:6 at most.

The copper salt of phytic acid of the present invention can be obtained by reacting an inorganic copper salt or an organic copper salt with the aforementioned phytic acid.

As the inorganic copper salt used for the reaction, copper sulfate, copper chloride, copper carbonate and so forth can be mentioned. While the amount of the inorganic copper salt varies depending on the type of the inorganic copper salt to be used, it is preferably used in an amount of 0.5–6.0 molar equivalents, more preferably 1.5–2.5 molar equivalents on the phosphoric acid groups of phytic acid.

When an organic copper salt is used, copper salts of carboxylic acids such as copper acetate, copper formate, copper stearate, copper tartrate, copper citrate and copper benzoate can be used, and copper acetate is preferred.

While the amount of the organic copper salt varies depending on the type of the organic copper salt to be used, it is preferably used in an amount of 0.5–6.0 molar equivalents, more preferably 1.5–2.5 molar equivalents on the phosphoric acid groups of phytic acid.

The reaction temperature varies depending on the kind of the reactants and so forth. However, it is generally 10–90° C., preferably 20–30° C.

The reaction time is a time required for full dissolution of the reactants, and it varies depending on the kinds of the reactants and so forth. It is usually around 0.5 to 4 hours.

Treatments after the reaction can be performed by adding dropwisely the reaction mixture into an organic solvent that is miscible with water at an arbitrary ratio after the completion of the reaction, and collecting deposited copper salt of phytic acid by, for example, filtration.

The organic solvent that is miscible with water at an arbitrary ratio may be a poor solvent that causes deposition of the copper salt of phytic acid after the completion of the reaction. Examples thereof include lower alcohols such as methanol, ethanol, n-propanol and isopropanol, acetonitrile, acetone, dimethylformamide, dimethyl sulfoxide, tetrahydrofuran, mixed solvents of these and so forth.

The solid obtained as described above may be, for example, washed with a solvent such as alcohols, as required.

<2> Near Infrared Absorber

The present invention also provides a near infrared absorber comprising the aforementioned copper salt of phytic acid.

Since the copper salt of phytic acid of the present invention also has ability to absorb lights of ultraviolet wavelength range, it can also serve as an ultraviolet absorber.

The near infrared absorber of the present invention can be made as, for example, a film that can be obtained by adding a suitable amount of the copper salt of phytic acid of the present invention to a synthetic resin such as vinyl resin. This film is preferably a transparent film.

Further, since the copper salt of phytic acid of the present invention shows extremely high solubility in water, the copper salt of phytic acid can also be used by being dissolved it in water. In this case, the near infrared absorber may be, for example, a filter that comprises an aqueous solution of the copper salt of phytic acid which is sealed up between two transparent plates (of which material may be a synthetic resin such as polycarbonate, acrylic resin and vinyl chloride, or plate glass) disposed so as to face to each other.

By adhering the aforementioned film or filter to window glass of buildings, it becomes possible to shield lights of near infrared wavelength range. Since the compound of the present invention does not shield visible lights unlike curtains or blinds, it can shield lights of near infrared wavelength range without reducing indoor brightness.

Furthermore, if the film or filter is used as a film or filter for cultivation in plant cultivation, good growing power of plants can be obtained, since the film or filter shields heat rays and ultraviolet rays harmful to plant growth, but does not shields visible lights required for plant growth.

These film and filter can be utilized also as an optical filter such as filter for light measurement that adjusts characteristics of photodiodes.

EXAMPLE

The present invention will be more specifically explained with reference to the following example. However, the present invention is not limited by the following example.

Example 1

Into 13.7 g of 50% phytic acid solution (Tokyo Kasei Co., Ltd.), 4.15 g of copper acetate monohydrate (Wako Pure Chemical Industries, Ltd.) was added and fully dissolved by stirring. This solution was added dropwisely little by little to a vigorously stirred mixture of 400 ml of isopropanol and 50 ml of methanol. After deposition of crystals, the crystals were filtered under reduced pressure by using a Kiriyama funnel, and washed several times with isopropanol to obtain solid showing slight viscosity. The solid was wetted with methanol, and pulverized into fine powder with a spatula. The powder was added with methanol again, and stirred for 30 minutes to wash it. The suspension was filtered again by using a Kiriyama funnel and dried in vacuo to obtain 6.60 g of near infrared absorbing composition as blue powder.

The ratio of copper to phosphoric acid groups in this powder was analyzed, and it was found to be 1:2.45.

This powder was dissolved in ion-exchanged water at a concentration of 20 mg/ml, and absorption spectrum of the solution was determined. The result is shown in FIG. 1.

The compound of the present invention, of which absorption spectrum is shown in FIG. 1, does not substantially show absorption in the region of 400–600 nm, which corresponds to visible light, but shows absorption over a wide range of 750–1100 nm.

According to the present invention, there can be provided a near infrared absorbing compound that hardly absorbs lights of visible light wavelength range, but strongly broadly absorbs lights of near infrared wavelength range.

Further, the compound of the present invention is highly water-soluble. Therefore, it can be utilized for aqueous filter devices by being dissolved in water at a high concentration to provide such devices absorbing lights of near infrared rays but well transmitting visible lights.

Furthermore, the compound of present invention can be produced at a low cost, since it is produced from a raw material abundantly present in nature.

The present invention also provides a near infrared absorber comprising the compound of the present invention.

Having thus described the present invention, it will be obvious that the same may be practiced in various ways. Such variations are not to be regarded as departure from the spirit and scope of the invention, and all such modifications would be obvious for one skilled in the art intended to be included within the scope of the following claims.

What is claimed is:

1. A near infrared absorber comprising a copper salt of phytic acid as a near infrared absorbing compound and resin so as to provide the near infrared absorber in the form of film for absorbing near infrared wavelength range, wherein the copper salt of phytic acid consists of $Cu^{2+}$ and phytic acid at a molar ratio of $Cu^{2+}$ to phytic acid being 2:1 or higher.

2. The near infrared absorber according to claim 1, wherein the copper salt of phytic acid is obtainable by reacting an inorganic copper salt or an organic copper salt with phytic acid.

3. The near infrared absorber according to claim 1, wherein the organic copper salt is a copper salt of a C2–C8 carboxylic acid.

* * * * *